(12) United States Patent
Gibson et al.

(10) Patent No.: US 6,671,554 B2
(45) Date of Patent: Dec. 30, 2003

(54) ELECTRONIC LEAD FOR A MEDICAL IMPLANT DEVICE, METHOD OF MAKING SAME, AND METHOD AND APPARATUS FOR INSERTING SAME

(75) Inventors: Scott R. Gibson, Granada Hills, CA (US); Rajiv Shah, Rancho Palo Verde, CA (US); Edward Chernoff, Frazier Park, CA (US); Charles Byers, Canyon Country, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 0 days.

(21) Appl. No.: 10/033,720

(22) Filed: Dec. 27, 2001

(65) Prior Publication Data

US 2003/0050680 A1 Mar. 13, 2003

Related U.S. Application Data

(60) Provisional application No. 60/317,870, filed on Sep. 7, 2001.

(51) Int. Cl.[7] .......................... A61N 1/375; H01R 13/15
(52) U.S. Cl. ........................ 607/37; 439/909; 439/827
(58) Field of Search ............................... 607/116, 2, 37, 607/122, 123, 126; 439/827, 370, 345, 775, 816, 825, 909; 600/374, 375, 377, 395, 396

(56) References Cited

U.S. PATENT DOCUMENTS

| 4,240,438 | A | | 12/1980 | Updike et al. |
|---|---|---|---|---|
| 4,469,104 | A | * | 9/1984 | Peers-Trevarton ........... 607/27 |
| 4,479,796 | A | | 10/1984 | Kallok |
| 4,484,987 | A | | 11/1984 | Gough |
| 4,568,335 | A | | 2/1986 | Updike et al. |
| 4,628,928 | A | | 12/1986 | Lowell |
| 4,650,547 | A | | 3/1987 | Gough |
| 4,703,756 | A | | 11/1987 | Gough et al. |
| 4,757,022 | A | | 7/1988 | Shults et al. |
| 4,771,772 | A | | 9/1988 | DeWitt |
| 4,848,346 | A | * | 7/1989 | Crawford ...................... 607/37 |
| 4,890,620 | A | | 1/1990 | Gough |
| 4,911,168 | A | | 3/1990 | Davis |
| 4,934,366 | A | | 6/1990 | Truex et al. |
| 4,994,167 | A | | 2/1991 | Shults et al. |
| 5,016,646 | A | * | 5/1991 | Gotthardt et al. ........... 607/122 |
| 5,046,965 | A | * | 9/1991 | Neese et al. ................. 439/372 |
| 5,070,605 | A | | 12/1991 | Daglow et al. |

(List continued on next page.)

FOREIGN PATENT DOCUMENTS

WO    WO 01/01851 A1    1/2001

OTHER PUBLICATIONS

PCT International Search Report as issued in International Application No. PCT/US02/28014, Mailing date Dec. 19, 2002.

*Primary Examiner*—Kennedy Schaetzle
(74) *Attorney, Agent, or Firm*—Foley & Lardner

(57) ABSTRACT

An implantable coaxial lead includes a cable with male and female connectors. The cable includes inner and outer helical coils separated by an inner insulator tube, with an outer insulator tube surrounding the outer helical coil. The male connector includes an outer conductive cylinder, a conductive pin and an insulator molded in between. For increased strength, a braided cylinder, infused with rubber, is included at the juncture of the male connector and the cable. The female connector includes a cylinder formed by two conducting body elements and an intervening insulating body element. The female connector includes respective conductive tension elements configured to engage the male connector. A first seal is provided between the conductive tension members for electrical isolation and tactile feedback. An insertion tool includes a cylinder with a hollow bore and detachable head, and a rod for pulling the lead through the cylinder.

75 Claims, 11 Drawing Sheets

U.S. PATENT DOCUMENTS

| | | |
|---|---|---|
| 5,094,951 A | 3/1992 | Rosenberg |
| 5,231,996 A | 8/1993 | Bardy et al. |
| 5,266,688 A | 11/1993 | Rosenberg |
| 5,328,460 A | 7/1994 | Lord et al. |
| 5,413,595 A * | 5/1995 | Stutz, Jr. .................... 607/37 |
| 5,497,772 A | 3/1996 | Schulman et al. |
| 5,522,874 A * | 6/1996 | Gates ........................ 607/127 |
| 5,534,025 A | 7/1996 | Moussy |
| 5,593,852 A | 1/1997 | Heller et al. |
| 5,649,974 A | 7/1997 | Nelson et al. |
| 5,660,163 A | 8/1997 | Schulman et al. |
| 5,665,093 A | 9/1997 | Atkins et al. |
| 5,667,983 A | 9/1997 | Abel et al. |
| 5,696,314 A | 12/1997 | McCaffrey et al. |
| 5,707,502 A | 1/1998 | McCaffrey et al. |
| 5,711,868 A | 1/1998 | Maley et al. |
| 5,728,281 A | 3/1998 | Holmstrom et al. |
| 5,741,211 A | 4/1998 | Renirie et al. |
| 5,741,319 A | 4/1998 | Woloszko et al. |
| 5,770,028 A | 6/1998 | Maley et al. |
| 5,773,270 A | 6/1998 | D'Orazio et al. |
| 5,791,344 A | 8/1998 | Schulman et al. |
| 5,804,048 A | 9/1998 | Wong et al. |
| 5,919,216 A | 7/1999 | Houben et al. |
| 5,932,175 A | 8/1999 | Knute et al. |
| 5,941,906 A | 8/1999 | Barreras, Sr. et al. |
| 5,965,380 A | 10/1999 | Heller et al. |
| 5,985,129 A | 11/1999 | Gough et al. |
| 5,992,211 A | 11/1999 | Skrtic |
| 6,001,067 A | 12/1999 | Shults et al. |
| 6,002,954 A | 12/1999 | Van Antwerp et al. |
| 6,027,479 A | 2/2000 | Alei et al. |
| 6,049,727 A | 4/2000 | Crothall |
| D424,696 S | 5/2000 | Ray et al. |
| D426,638 S | 6/2000 | Ray et al. |
| 6,093,167 A | 7/2000 | Houben et al. |
| 6,103,033 A | 8/2000 | Say et al. |
| 6,120,676 A | 9/2000 | Heller et al. |
| 6,122,536 A | 9/2000 | Sun et al. |
| 6,125,290 A | 9/2000 | Miesel |
| 6,125,291 A | 9/2000 | Misel et al. |
| 6,134,459 A | 10/2000 | Roberts et al. |
| 6,135,978 A | 10/2000 | Houben et al. |
| 6,144,866 A | 11/2000 | Miesel et al. |
| 6,159,240 A | 12/2000 | Sparer et al. |
| 6,162,611 A | 12/2000 | Heller et al. |
| 6,163,723 A | 12/2000 | Roberts et al. |
| 6,175,752 B1 | 1/2001 | Say et al. |
| 6,198,952 B1 | 3/2001 | Miesel |
| 6,201,980 B1 | 3/2001 | Darrow et al. |
| 6,248,080 B1 | 6/2001 | Miesel et al. |
| 6,251,260 B1 | 6/2001 | Heller et al. |
| 6,261,280 B1 | 7/2001 | Houben et al. |
| 6,268,161 B1 | 7/2001 | Han et al. |

* cited by examiner

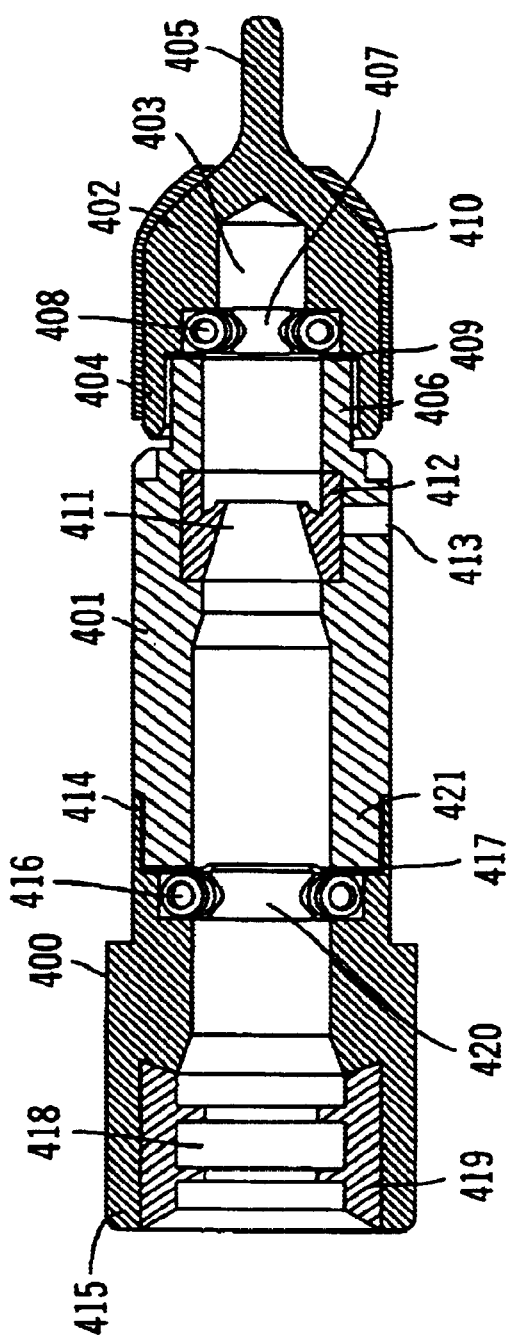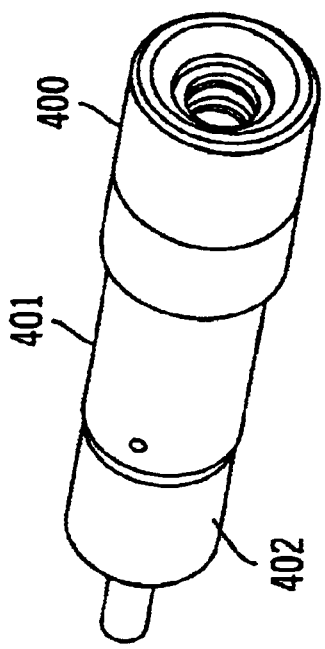
FIG. 4A
FIG. 4B

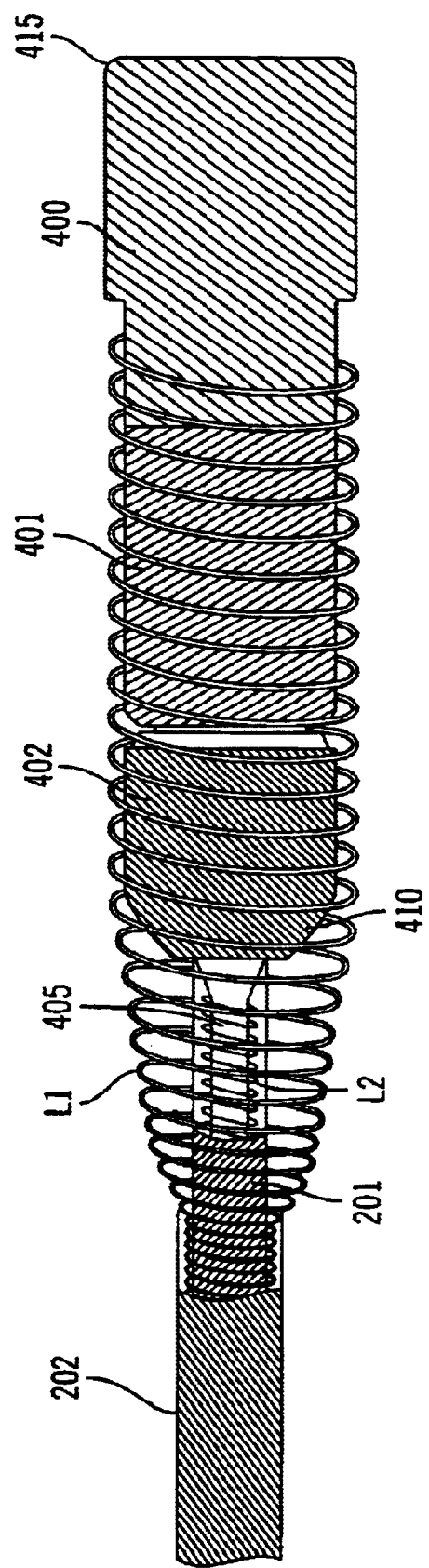

ELECTRONIC LEAD FOR A MEDICAL IMPLANT DEVICE, METHOD OF MAKING SAME, AND METHOD AND APPARATUS FOR INSERTING SAME

CROSS-REFERENCE TO RELATED APPLICATIONS

Embodiments of the present invention claim priority from a U.S. Provisional Application entitled "Electronic Lead for a Medical Implant Device, Method of Making Same, and Method and Apparatus for Inserting Same," Serial No. 60/317,870, filed Sep. 7, 2001, the contents of which are incorporated by reference herein.

FIELD OF THE INVENTION

The present invention relates generally to the field of medical devices, and, more specifically, to electronic leads for implants and tools for using such electronic leads.

RELATED ART

Electronic implant devices are used in the medical profession to monitor health processes, such as glucose levels and heart activity, and to control or stimulate health processes, such as controlling heart rate and stimulating muscle function. Examples of implant devices include glucose sensors, pacemakers, muscle stimulators, and the like.

Implanted systems may include multiple devices connected for communication. In this case, a mechanism for electrical transmission between these devices is needed, whether for communication of data, power or both. Typically, due to power and size constraints, electrical transmission is relegated to a single pair of conductors. Two conductors are typically sufficient to send ground and supply voltages from a power supply to an implant device, or, for communication of data between two or more devices.

Because implantable leads are designed to be implanted in the subcutaneous tissue of a patient's body, the dimensions of such leads can have an impact on the level of comfort of the implant patient and the external appearance of the implant path. Also, the path of the lead implant may be substantially determined by the other devices within the implanted system, limiting options for selecting a least offensive implant path. Typically, a lead of relatively small dimensions and, in particular, a relatively small diameter dimension, will minimize patient discomfort and noticeable protrusions along the implant path. Accordingly, there is a demand in the industry for minimizing the diameter dimension of implantable electronic leads, particularly in sensor applications where, for example, the size of a glucose sensor is of the same order as the diameter of the electrical lead.

Small devices like the glucose sensor may be implemented with no power source of their own, and rely on power extracted from the data signal itself. As power levels are typically low to begin with, it is important that the electrical lead have a high conductivity value to minimize power attenuation over the length of the lead. The lead should also be sufficiently strong and flexible to resist breaking due to any stresses placed on the lead by the insertion process during the implant operation, as well as stresses caused by movement or pressure of the patient's body during normal activities. Unfortunately, the need for strength, flexibility and high conductivity often limits how small the diameter of an electrical lead can be made.

Other problems with implantable leads concern the connectors used to couple the leads to the implanted devices. For example, most connector structures are of greater diameter than the lead itself. This can cause extra trauma during insertion as these nonuniform structures catch and tear in the body tissues. Further concerns are with the integrity of the connections achieved by the connectors. It is important that the connectors not become disconnected during use. Connection integrity is typically ensured by complicated cam structures or external screws which the surgeon must manipulate during the implant process to lock the connection. Also, fluids and other matter from the exterior implant environment can penetrate the connectors, resulting in a short between conductors. Pacemaker leads have used a single rubber O-ring to seal out fluids. However, there is a need for connectors that can provide a more efficient seal to inhibit such short circuits from occurring.

Finally, the junction between the cable and the connectors is often placed under greater amounts of stress than other portions of the lead. Therefore, the lead is more likely to fail at that point. Pacemaker leads have tried to overcome this weakness in the cable by molding large ball-like or disk-like rubber structures around the lead at those points to resist excessive flexure. Such external structures only serve to widen the diameter of the cable at those points, generate unwanted protrusions, and complicate insertion procedures.

Thus, there remains a demand in the industry for new and improved electrical lead structures that have reduced diameter dimensions, yet which do not compromise other operational characteristics, such as the strength to resist stress and the conductivity to minimize attenuation. Further, lead structures are needed that minimize diameter-related anomalies caused by connectors and stress relieving structures, and that provide secure connections without requiring complicated manipulations by a surgeon during insertion.

SUMMARY OF THE DISCLOSURE

Embodiment of the present invention relate generally to implant devices having one or more lead cables for the transmission and/or reception of electrical signals between two or more electronic devices in a medical implant environment. Particular embodiments relate to cables, connectors and tools for such devices and methods of making and using the same, which address one or more of the concerns and demands in the industry as noted above.

Embodiments of the invention may employ cable structures that reduce the diameter and improve the strength of the lead, as compared to prior cable technologies. In this manner, smaller leads may be used in implant procedures to reduce the initial physical trauma of the implant procedure, and the continuing discomfort and physical trauma caused by the constant presence of the implanted lead, without compromising the strength and conductivity of the lead. Embodiments of the invention may also employ connector structures that simplify the operation and enhance the reliability of the lead connectors, as compared to prior connector configurations. Thus, implant leads may be connected quickly and easily, without sacrificing retention strength, circuit integrity or the surgeon's confidence that a connection was made. Further, embodiments of the invention may also employ insertion tools to minimize surgical trauma and maximize surgical efficiency, as compared to prior implant procedures. In this manner, leads may be implanted quickly and easily, without sacrificing safety. Various preferred embodiments may be particularly suited for implant environments. Other preferred embodiments may be employed in external (non-implant) environments.

A sensor lead according to an embodiment of the invention includes a coaxial cable structure, a female connector and a male connector. The cable structure includes an outer insulator tube containing an inner coil and an outer coil separated by an inner insulator tube. The inner and outer coils may be helical ribbon conductors that each represent a separate electrical channel. In some embodiments, the helical ribbon conductors include multiple adjacent wires configured in a ribbon strip that is twisted about a central axis. In this manner, a strong and conductive cable is formed that is also both thin and flexible. In some embodiments, each wire is made up of a highly conductive silver core surrounded by a durable cobalt alloy. According to one aspect of the invention, a tolerance value may be determined for maximum radial offsets by any one wire in a coil, to prevent stress points along the cable. Further, a nominal coil spacing distance may be determined to provide a desired balance of strength and flexibility.

A female connector according to an embodiment of the invention has a female connector body including two conductive body members separated by a middle insulator. The female connector body defines an inner cavity configured to accept a male connector via insertion. Within grooves along the interior walls of the connector body, the connector includes the following: respective conductive tension members electrically coupled to each of the conductive body members, and a seal molded into the middle insulator to electrically isolate the interiors of the conductive body members from each other. In some embodiments, the conductive tension members are implemented by toroidal springs oriented to apply radially directed tension onto respective conducting elements of the male connector for electrical conduction, as well as connection retention. Wear-resistant members may be used to prevent the conductive tension members from damaging the middle insulator. According to one aspect of the invention, the middle insulator may be formed of a resilient material, such as polysulfone. The middle insulator may then be coupled to each of the conductive body members using a friction fit, obviating any need for adhesives.

According to another aspect of the invention, the seal in the middle insulator is configured with an umbrella-shaped ridge for engaging a similar ridge on the male connector. In addition to providing a seal and additional retention force, the umbrella-shaped ridge may provide tactile feedback to a surgeon when the male and female connectors are firmly engaged, improving confidence in the connection. In a further aspect of the invention, a second seal may be provided near the mouth of the female connector body to engage the male connector and isolate the interior of the female connector from the outer implant environment, improving reliability of the connection. In some embodiments, the combined retention force of the conductive tension members and the intervening seals are sufficient to obviate any need for more complex retention mechanisms, allowing a simple unidirectional insertion process.

In yet a further aspect of the invention, the cable maintains a uniform diameter, but for where the cable joins the female connector. At this junction, the outer conducting coil wraps around the exterior of the female connector body to be electrically coupled to the exterior surface of one of the conducting body members. The female connector and the outer coil may then be overmolded with a protective insulating material. In some embodiments, suture holes or rings may be added to the female connector during the overmolding process.

A male connector according to an embodiment of the invention includes a conductive surface and a conductive pin configured to engage respective tension members of the female connector. An insulating member may be formed between the conductive surface and the conductive pin, and provides, in some embodiments, a ridge configured to engage the umbrella-shaped ridge of the female connector. In further preferred embodiments, the male connector is configured to have a diameter no greater than that of the lead cable.

In further embodiments of the invention, a flexible braided cylinder is used as a strengthening apparatus where the lead cable and the male connector are joined. During an overmolding process for the male connector, the braided cylinder is infused with molding material, such as silicon rubber, until the braided cylinder is generally the same diameter as the cable.

A lead implant process according to an embodiment of the invention utilizes an insertion tool to tunnel a desired lead path through the subcutaneous tissue of a patient. The insertion tool includes a rigid, elongated member with a hollow bore and a detachable bullet-shaped member or endpiece. A rod, having a connector member on one end, is configured to slide through the bore of the elongated member for purposes of connecting to the lead and drawing the lead into the elongated member.

In practice, according to one embodiment, a surgeon inserts the elongated member into a patient, for example, through a source incision near a first implant device. The elongated member is then guided through the subcutaneous tissue of the patient until the detachable bullet-shaped member exits a destination incision near a second implant device. The detachable member is removed to expose the connector member of the rod, and the lead is attached to the connector member. The surgeon may then draw the lead into the elongated member by pulling the rod through the hollow bore. Once the connector member is outside the bore, the lead is detached and the elongated member is removed from the patient, leaving the lead in place within the lead path formed by the insertion tool. The lead may then be connected to the implant devices and sutured in position.

Embodiments of the invention may employ any one or combination of aspects described herein for minimizing or reducing the required diameter of the cable structure, simplifying the operation and enhancing the reliability of the lead connectors, minimizing surgical trauma and maximizing surgical efficiency. In one preferred embodiment, all aspects described herein may be employed to result in a lead structure that is small, strong, reliable and easy to use.

These and other aspects and advantages of the invention will be apparent to one of skill in the art from the accompanying detailed description and drawings. Each of the above-noted aspects of the invention, as well as other aspects of the invention, may be practiced separately or in various combinations.

BRIEF DESCRIPTION OF THE DRAWINGS

FIG. 4A is a cross-sectional side view of a female connector in accordance with an embodiment of the invention.

FIG. 4B is a perspective view of a female connector in accordance with an embodiment of the invention.

FIG. 5 is a cross-sectional side view of a female connector coupled to a cable in accordance with an embodiment of the invention.

DETAILED DESCRIPTION OF THE PREFERRED EMBODIMENTS

The present invention relates generally to implantable leads for electronic medical implant devices, and to methods for making and using such leads. This description is not to be taken in a limiting sense, but is made merely for the purpose of illustrating the general principles of example embodiments of the invention. The scope of the invention is best defined by the appended claims. In the following description, numerous specific details are set forth to provide a more thorough description of one or more embodiments of the invention. It will be apparent, however, to one skilled in the art, that the invention may be practiced without these specific details. In other instances, well known features have not been described in detail so as not to obscure the invention. Though described herein as a sensor lead for medical implants and especially suited to that purpose, it will be apparent that embodiments of the invention are also applicable to internal and external medical applications other than sensor implants, as well as electronic lead applications outside of medicine.

Certain preferred embodiments of the invention relate to such sensor leads configured with a minimized diameter dimension, for example, to minimize trauma to the implant recipient (referred to herein as the patient), to improve the efficiency of the implant process and the tools with which the implant process may be performed and/or to improve the reliability of the implant apparatus. The term "patient" is intended to refer to the entity in which the implantable devices are implanted, whether or not the implant is carried out for medical purposes. Accordingly, the term "patient" is not to be construed as a reference or limitation to a medical context.

I. General Overview of Lead System

Figure 1:
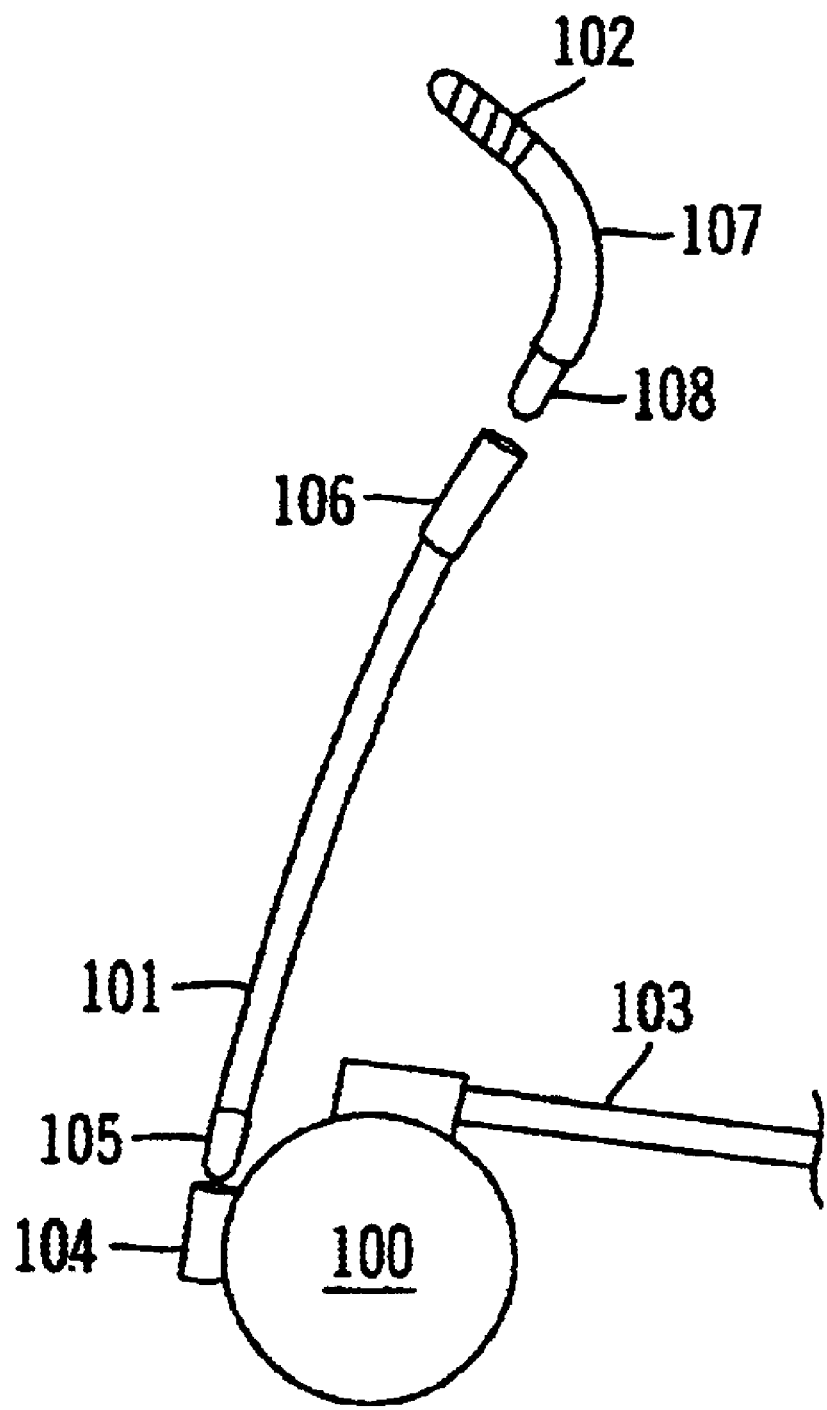
FIG. 1 is a diagram of a sensor lead used in a glucose sensor/pump application.

FIG. 1 is a diagram of a pump/sensor implant system utilizing a sensor lead in accordance with an embodiment of the invention. The system comprises a pump 100, a sensor lead 101 and a sensor 102. Pump 100 may be configured with a catheter 103 and a female connector port 104. Sensor lead 101 comprises a male connector 105 engaged with female connector port 104, and a female connector 106. Sensor 102 may be configured with a small lead 107 having a male connector 108 engaged with the female connector 106 of sensor lead 101.

The system described above may be configured to provide certain economies of design and materials when there is commonality between connectors. For example, male connector 105 and male connector 108 may be substantially identical, and, accordingly, female connector 106 and female connector port 104 may share substantially the same design and material components. This commonality of connectors provides time and cost savings, as well as flexibility in making new configurations without detailed redesign. For example, multiple leads may be daisy-chained within power limitations, or new devices may be inserted into the system more easily. One or more embodiments of the invention may employ such a commonality of connectors.

In determining a suitable form factor for the sensor lead 101, advantages may be found in the implementation of a lead having a uniform diameter of minimal size. In one or more embodiments of the invention, the entire lead, apart from the female connector 106, may have a diameter no greater than that of the outer insulator of the cable portion. As described in more detail below, embodiments of the sensor lead may be inserted from one incision and guided under the skin of the patient to a target location. In such embodiments, a uniform cross-sectional profile minimizes trauma to the tissue being penetrated in this manner, because the diameter of the initial insertion path need never change. Also, as will be discussed in accordance with one embodiment of the invention, a uniform profile permits the use of innovative insertion tools that minimize the complexities of the operation, reducing operating times and hence reducing the patient's exposure to complications on the operating table. Further, the reduced risk on the operating table may diminish the reluctance of a patient or doctor to have sensor leads and other implant devices replaced more frequently, resulting in fewer implant device failures.

As a further reduction in operating complexity, lead connectors in one or more embodiments of the invention may be unidirectional in nature, requiring only simple push/pull actions to engage or disengage an associated connector. Tactile feedback also may be provided so that a surgeon knows when a solid connection is made. Thus, reliable connections may be achieved without the use of set screws and cams of prior art connector technologies.

II. Elements of Sensor Lead

Elements of a sensor lead, according to an embodiment of the invention, may be considered in terms of three main components: the lead cable, the female connector, and the male connector.

A. Cable Structure

Figure 2A:
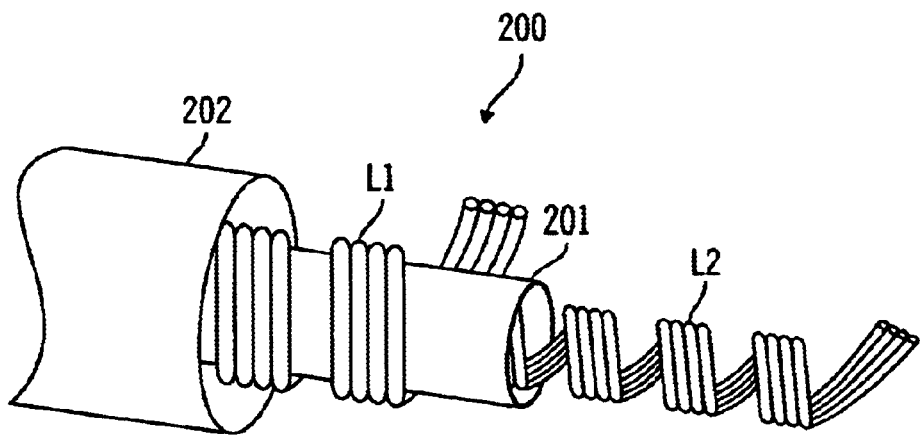
FIG. 2A is a partial cut-away side view of a sensor lead cable in accordance with an embodiment of the invention.

FIG. 2A is a partial cut-away side view of a sensor lead cable 200 in accordance with an embodiment of the invention. Sensor lead cable 200 comprises, for most of its length, an outer conductive coil L1 and an inner conductive coil L2, separated by an inner insulator tube 201, and covered by an outer insulator tube 202. The diameter of the cable may be constant throughout the length of the cable. In a further embodiment, the cable diameter may be generally constant, except near the female connector where outer coil L1 widens to encompass the female connector body. For better flexibility, the helical coils and insulator tubes may fit relatively loosely. Inner coil L2 rests loosely within the hollow interior of inner insulator tube 201, and outer coil L1 rests loosely inside of outer insulator tube 202.

In one embodiment, inner coil L2 may have an inner diameter of about 0.019" (19 mils) +/−0.002", with a wire thickness in the range of about 0.0025" +/−0.0005". Preferably, the fit between inner insulator tube 201 and outer coil L1 is loose (e.g., about 0.004" clearance). Outer coil L1 may have an inner diameter of about 0.045" +/−0.002", with a wire thickness of about 0.005". At the female connector, the inner diameter of outer coil L1 may be in the range of 0.175" to 0.185", and, in one embodiment, is about 0.179". Some or all of these dimensions may vary for other embodiments.

Each coil may be created by forming a ribbon strip of wires side by side, and then winding the ribbon strip into a helix. The use of multiple conductive wires in each helical coil provides for conductive redundancy in case one of the wires breaks. Also, with multiple wires coiled as a strip, conductance may be improved due to the parallel nature of the conductors, and cable parameters such as flexibility, strength and form factor (i.e., physical dimensions) may be optimized. The number of wires used in the coiled strip may be determined with consideration for the increased complexity of winding multiple wires into a coil within dimensional tolerances, as well as the reduction in spring-based flexibility as the number of windings is reduced to accommodate the number of wires. In one embodiment, each of the coils has four conducting wires. However, other numbers of wires may be used in other embodiments of the invention.

Figure 2B:
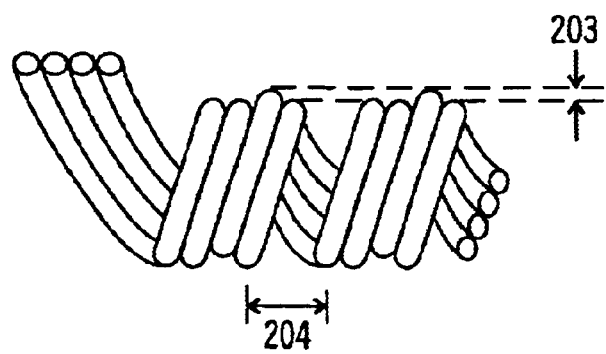
FIG. 2B is a side view of a coil showing wire radial offset tolerances in accordance with an embodiment of the invention.

For more reliable performance, one embodiment imposes certain tolerances on the winding of individual wires within the coils. The tolerance value determines how much the wires maintain a uniform radial profile after winding. This tolerance is illustrated in FIG. 2B as the maximum radial offset 203 of any one wire winding relative to the rest of the wires. One reason for establishing an offset tolerance value is because larger variations in the radial profile of the windings can create an undesirable stress point in the coil, causing failure of one or more windings and/or a short between coil L1 and coil L2 due to wear in the inner insulator tube at the stress point. According to one embodiment, a maximum radial offset may be equal to one wire diameter maximum. In one embodiment, for example, a coil with a thickness of about 0.006", may have a radial offset tolerance of 0.005". This tolerance value may differ for other embodiments based on, for example, acceptable cable failure rates, strength of materials, and other application parameters.

In addition to the offset tolerance value, one or more embodiments may have a desired value for the coil spacing distance 204 to achieve a certain balance between flexibility and strength. Wrapping a coil more tightly enhances the strength of the coil structure, but lessens the flexibility, because the coil has less room to compress and flex between coils. The desired value for coil spacing distance 204 in a sensor lead may vary for different embodiments and application parameters (e.g., the number of wires in the ribbon strip, the diameter of the coil, the strength of the material used to form the wires, the flexing needs of the implant location, etc.). For example, in one embodiment, the desired value for coil spacing distance 204 may be 0.030" to 0.035".

Figure 3:
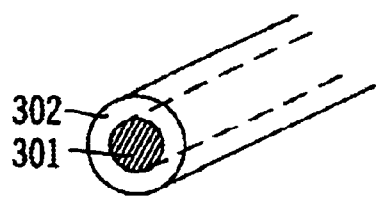
FIG. 3 is a cross-sectional view of a single wire used in a sensor lead cable in accordance with an embodiment of the invention

FIG. 3 is a cross-sectional view of an individual wire 300 used in accordance with one embodiment of the invention to form outer coil L1 and inner coil L2 in the lead cable. Wire 300 may be an unshielded conductive cylinder containing an Ag (silver) core 301 with an outer layer 302 of MP-35N material (cobalt alloy). The silver core 301 provides for a higher conductivity wire, whereas the outer MP-35N layer 302 provides a conductive, yet highly corrosive-resistant shell. No further shielding may be necessary as contact between wires of a single coil does not compromise performance, and the inner insulator tube may provide for electrical isolation between the inner and outer coils.

Though the wire construction of the described embodiment provides for performance characteristics well-suited to medical applications, other wire designs may be utilized in alternative embodiments. In addition, other embodiments may employ conductors composed of other suitable conductive materials, including, but not limited to gold, copper, or the like, covered by a layer of MP-35N or other material or uncovered.

B. Female Connector

The female connector of the sensor lead may be a coaxial coupling mechanism designed to mechanically and electrically engage a complimentary male connector. In one embodiment, a unidirectional coupling may be designed such that the male connector may be simply pushed into the female connector to establish the coupling. To disengage the coupling, the male connector may be pulled straight away from the female connector. To maintain integrity of the coupling when the male and female connectors are engaged, friction force may be used for a secure fit, rather than set screws, cam elements or locking tools utilized in prior art connectors. The friction fit may be provided by sealing elements that resist unidirectional movement, as well as internal tension mechanisms that serve to pinch the male connector in place.

For a unidirectional connector, it may be desirable to have a maximum insertion force needed to establish engagement, as well as a minimum retention force sufficient to maintain engagement. If too much insertion force is required, insertion may overstress the cable and connector elements, whereas if too little retention force is provided, the connectors may disengage during use. The European standards for screwless pacemaker connectors require a maximum insertion force of fourteen Newtons and a minimum retention force of five Newtons. Embodiments of a connector design described herein may be configured to meet such requirements.

FIG. 4A is a cross-sectional side view of a female connector in accordance with an embodiment of the invention. In general, the body of the female connector defines a cylindrical cavity into which the male connector is inserted. The female connector may be substantially symmetric about its central axis, though such may not be the case in all embodiments. The body of the female connector comprises three main elements: conductive body member 400, middle insulator 401, and conductive body member 402. Conductive body members 400 and 402 conduct the electrical signals of coils L1 and L2, respectively. A perspective view of the female connector of FIG. 4A is provided in FIG. 4B, showing the outer surfaces of conductive body member 400, middle insulator 401 and conductive body member 402.

In one embodiment, conductive body members 400 and 402 may be contact rings or cylinders, though other connector embodiments may use different configurations or profiles (e.g., generally cubic rather than generally cylindrical). Conductive body members 400 and 402 may be formed of any conductive material (preferably of surgical quality for medical applications), such as, but not limited to, steel, or the like. Conductive elements may also be fabricated from suitable nonconducting materials over which a coating or layer of conductive material is applied, or through which a conductive medium is passed.

Middle insulator 401 may be formed from any insulating material. However, in one embodiment, middle insulator 401 may be formed of a suitably resilient material, such as, but not limited to, polysulfone, or the like. In such an embodiment, the resilience of the middle insulator 401 is used to secure conductive body members 400 and 402 to middle insulator 401 without the need for adhesives. This is an advantage, as glues can be soluble, and thus prone to failure in an implant environment. The connector elements may be machined to be stress-free with tight tolerances, allowing the female connector to be fitted together and secured by an overmolding of an insulating material, such as, but not limited to, silicon rubber, or the like.

Referring back to FIG. 4A, in one embodiment, conductive body member 402 may be a generally rigid, cylindrical structure defining a cavity 403 configured to accept the conducting tip of a male connector. A rim 404 of conductive body member 402 defines an opening to cavity 403 into which a first end 406 of middle insulator 401 may be fitted. Conductive body member 402 tapers closed around cavity 403, extending a narrow stem or finger 405 of conductive material away from cavity 403, along a central axis of the connector. To permit the outer conductive coil L1 to encircle the female connector without shorting to conductive body member 402, rubber molding 410 may be formed around the exterior surface of conductive body member 402, leaving extended stem 405 exposed.

Inside of cavity 403, an annular groove 407 may be formed on the interior surface of conductive body member 402. Groove configurations other than annular may also be implemented, particularly in embodiments where cavity 403 may not be generally cylindrical.

Annular groove 407 contains a conductive tension member 408. Conductive tension member 408 may be any conductive apparatus that exerts a tension force radially inward, such as, but not limited to, a toroidal spring. Conductive tension member 408 may be made from any of the aforementioned conductive materials (e.g., steel), and may be configured to provide one or more of the following functions: swiping the conductive tip of a male connector to provide a cleaner contact; gripping or pinching the tip of a male connector for extra retention force; guiding the male connector for a secure, centered fit; and providing an electrical coupling between the conductive tip of a male connector and conductive body member 402. The cylindrical rim of middle insulator 401 may act to secure conductive tension member 408 in annular groove 407.

Middle insulator 401 may be a generally cylindrical, non-conducting structure having first end 406 and second end 421 formed to engage conductive body member 402 and conductive body member 400, respectively, with an insertion fit. The inner bore of middle insulator 401 has an annular cavity 411 containing a seal 412, configured to electrically isolate the interior of conductive body element 402 from the interior of conductive body element 400. Seal 412 may be formed from any generally flexible insulating material, such as, but not limited to, silicon rubber, or the like. A hole 413 may be provided in middle insulator 401 to allow for venting during molding of seal 412. In one embodiment, seal 412 may be umbrella-shaped (or may have an umbrella-shaped ridge), to engage a corresponding umbrella-shaped projection on the male connector. The umbrella-shaped seal 412 will be described later in more detail with reference to the male connector.

Conductive body member 400 may be a generally rigid, cylindrical conducting structure having an inside annular rim 414 configured to engage second end 421 of middle insulator 401, and an outside rim 415 defining an opening configured to receive the male connector. Conductive body member 400 may be composed of, or coated with, any suitable conducting material, including, but not limited to, steel, or the like. Within the hollow bore of conductive body member 402 and generally adjacent to inside rim 414, conductive body member 402 may have an annular groove 420 configured to contain a second conductive tension member 416, similar to conductive tension member 408. The function of conductive tension member 416 may be similar to that of conductive tension member 408, though applied with respect to the surface of the male connector corresponding to conductive coil L1. The cylindrical rim of middle insulator 401 may act to secure conductive tension member 416 in annular groove 420.

To inhibit erosion of the resilient material of middle insulator 401 by either of the conductive tension members, a first wear-resistant member 409 may be fitted into annular groove 407, between conductive tension member 408 and first end 406 of middle insulator 401. A second wear-resistant member 417 may be fitted into annular groove 420, between conductive tension member 416 and second end 421 of middle insulator 401. In one embodiment, wear-resistant members 409 and 417 are generally annular in shape, and formed of any suitable wear-resistant material, such as, but not limited to, steel, or the like. A steel washer is one example of a possible embodiment of a wear-resistant member. In other embodiments, each wear-resistant member may be implemented as part of the respective adjacent conductive body member, e.g., as an annular ridge of the respective conductive body member, which separates the conductive tension member from middle insulator 401.

A second annular groove or recess 418 within the bore of conductive body member 400 may be located generally adjacent to outside rim 415. Recess 418 may be configured to contain a seal 419 formed of a ring of flexible material, such as molded silicon rubber, or other suitable materials. Rear seal 419 may be configured with two radially-directed, raised ridges that physically engage the shaft of the male connector upon insertion, providing a double seal to electrically isolate the interior of conductive body element 400 from the outer implant environment. In one embodiment, rear seal 419 may be fitted within recess 418 and secured during an overmolding process. In addition, or as an alternative, rear seal 419 may be glued in place.

FIG. 5 illustrates a configuration for joining the sensor lead cable to the female connector, in accordance with an embodiment of the invention. Coils L1 and L2 and inner insulator tube 201 may be extended beyond the edge of outer insulator tube 202 to expose outer coil L1. Inner coil L2 may encircle extended stem 405 of conductive body member 402 to establish an electrical connection, e.g., via welding of coil L2 to stem 405. Inner insulator tube 201 abuts rubber molding 410, electrically insulating inner coil L2 and stem 405. The diameter of the exposed portion of outer coil L1 is expanded to wrap around and across the outer surfaces of conductive body member 402 and middle insulator 401. Outer coil L1 is coupled to the outer surface of conductive body member 400, e.g., via welding or other suitable mechanism, to establish an electrical connection.

Inner insulator tube 201, molding 410 and middle insulator 401 insulate conductive body member 402 from outer coil L1, preventing an electrical short between opposing contacts. To protect the outer surface of the female connector, as well as exposed outer coil L1, the entire female connector, from outside rim 415 to the edge of outer insulator tube 202 (and slightly beyond) may be overmolded with a suitable protective insulating material, such as, but not limited to, silicon rubber.

Figure 6:
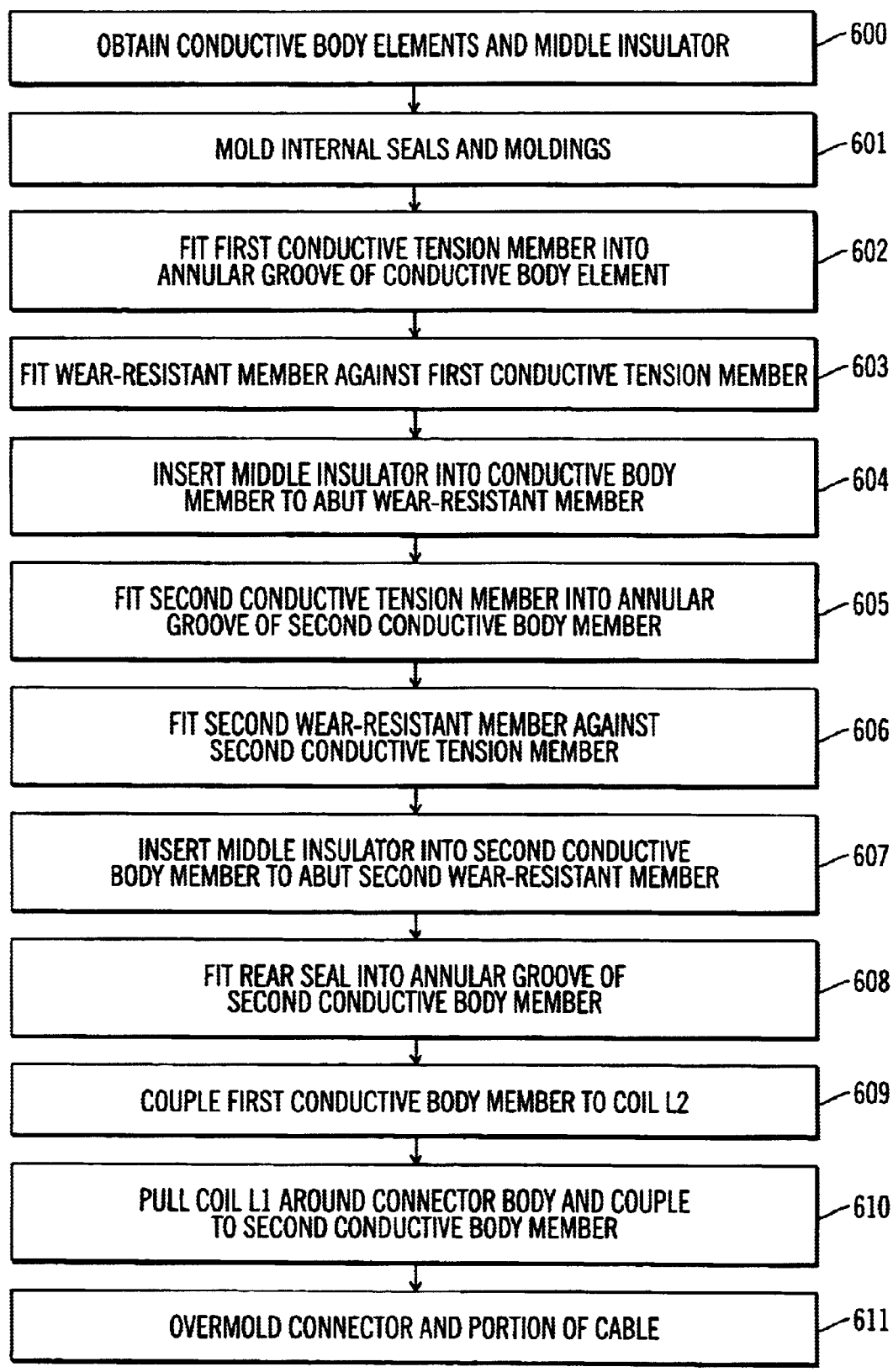
FIG. 6 is a flow diagram of a process for forming a female connector in accordance with an embodiment of the invention.

FIG. 6 is a flow diagram illustrating a procedure for fabricating a female connector in accordance with an embodiment of the invention. It will be understood by one skilled in the art that certain steps in the disclosed process may be performed in different order or in parallel with other steps without departing from the scope of the invention. Also, other embodiments may be fabricated according to other procedures.

In step 600, conductive body members 400 and 402 and insulator 401 are obtained. For example, conductive body members 400 and 402 may be fabricated or machined from steel, or other suitable conductive material, or formed from a suitable nonconductive material and coated with a conductive material. Middle insulator 401 may be molded from a nonconductive material that is preferably generally resilient, such as polysulfone, or other suitable resilient material. In step 601, the internal seals and insulator moldings are molded from silicon rubber or other suitable insulating material. Molding 410 is formed around the outer surface of conducting body member 402, and seal 412 is molded inside annular cavity 411 of middle insulator 401. A hole may be provided from cavity 411 to the outer surface of middle insulator 401, to allow seal 412 to vent during molding. Rear seal 419 may be either molded into recess 418 of conductive body member 400, or molded separately and then fitted into conductive body member 400.

In step 602, conductive tension member 408 is fitted into groove 407 of inner contact ring 402. Wear-resistant member 409 may be fitted against conductive tension member 408, in step 603, as wear protection for middle insulator 401. In step 604, first end 406 of middle insulator 401 is inserted into rim 404 of conductive body member 402 to abut wear-resistant member 409. Conductive body member 402 and middle insulator 401 may be machined to have tight tolerances and, thus, a snug, friction fit.

In step 605, conductive tension member 416 is fitted into groove 420 of conductive body member 400. Wear-resistant member 417 may be fitted against spring 416, in step 606. In step 607, second end 421 of middle insulator 401 is inserted into inside rim 414 of conductive body member 400 to abut wear-resistant member 417. In step 608, if not already molded in place, rear seal 419 may be fitted into recess 418 of conductive body member 400, and optionally glued into place with adhesive.

With the three main components of the female connector assembled as described, the cable may be fitted to the connector as follows. In step 609, stem 405 of conductive body member 402 may be inserted inside of inner coil L2, and welded, or otherwise electrically coupled, to coil L2. Inner insulator tube 201 is pulled over coil L2 to abut rubber molding 410. In step 610, exposed outer coil L1, with its expanded diameter, may be drawn around the outer surfaces of conductive body member 402 and middle insulator 401 to be welded, or otherwise electrically coupled, to the outer surface of conductive body member 400 (e.g., at or near the position corresponding to the inner surface position of conductive tension member 416). In step 611, the female connector (from outside rim 415) and an adjacent portion of the sensor cable may be overmolded with silicon rubber, or other suitable durable insulation material, for electrical and mechanical isolation from the outer implant environment. During this overmolding step, labels may be added to the sensor lead, as well as suture holes and/or rings, to assist in stabilizing the sensor lead within the patient's tissue.

C. Male Connector

In one embodiment of the invention, the male connector of the sensor lead may be a pin-based structure with dual conducting surfaces that align with the conductive tension members of the female connector previously described. The diameter of the cable and the male connector may be substantially the same in one or more embodiments of the invention, for easier implantation as described later in this specification. As with the female connector, all elements may be substantially symmetrical about the connector's central axis. Also, in accordance with one or more embodiments of the invention, strengthening apparatus may be attached to the cable near the male connector to avoid stress faults at that point in the sensor lead. It will be understood by one skilled in the art that other embodiments of the invention may forego such strengthening apparatus, or use alternate forms of strengthening apparatus, without departing from the scope of the invention.

Figure 7:
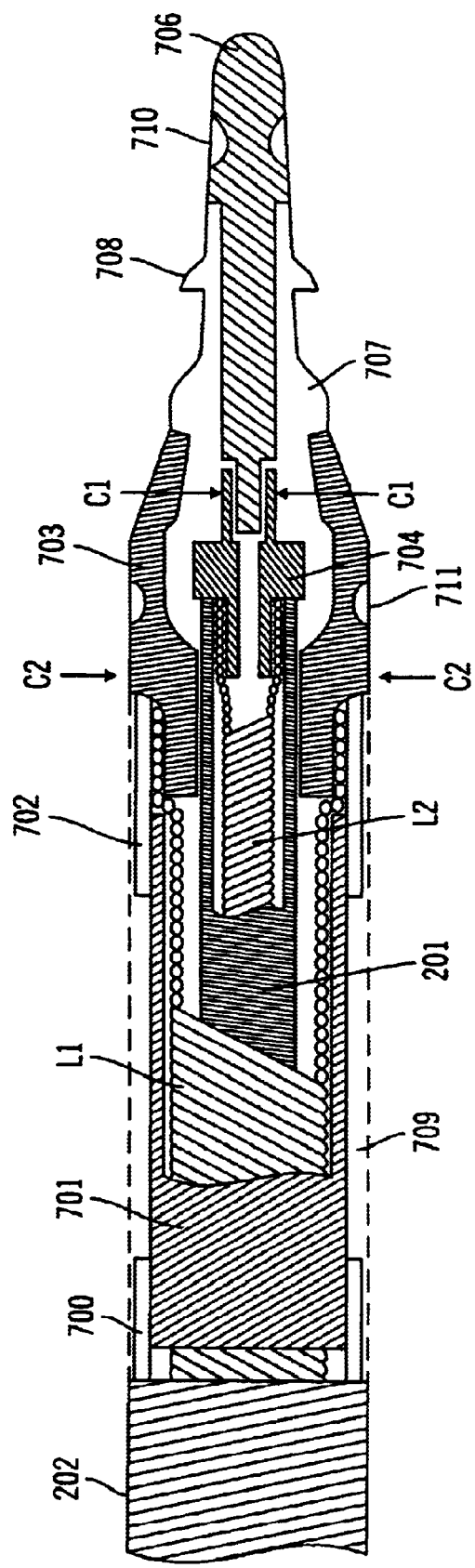
FIG. 7 is a cross-sectional side view of a male connector in accordance with an embodiment of the invention.

FIG. 7 is a cross-sectional side view of a male connector attached to a sensor lead cable in accordance with one embodiment of the invention. Where the cable attaches to the male connector, the cable may be passed through a strengthening apparatus comprising a braided tube 701 coupled at either end to rear ring 700 and front ring 702. Braided tube 701 may be constructed of steel mesh, or other suitably durable and flexible mesh material, through which a durable molding medium, such as silicon rubber, can penetrate during a molding process. In one embodiment, the threads of the mesh may preferably be attached to rings 700 and 702 to achieve successful connections for at least about eighty-percent of the threads. For example, in the case of steel mesh, the threads might be connected to rings 700 and 702 via spot-welding. In one embodiment, outer coil L1, inner insulator tube 201 and inner coil L2 are passed through the braided tube formed of elements 700–702, whereas outer insulator tube 202 is cut off where tube 202 abuts rear ring 700.

A cylindrical conductive surface such as outer contact ring 703 of the connector may be configured with a rearward rim that fits within and against the forward rim of front ring 702. Outer coil L1 may be wrapped around the rearward rim of outer contact ring 703 to which coil L1 is welded or otherwise electrically coupled. Inner insulator tube 201 and inner coil L2 may be passed into the inner cavity of outer contact ring 703. A cylindrical inner conductive ring 704 with narrowed rear and forward rims is located within the hollow interior of outer contact ring 703. The rear rim of inner conductive ring 704 is electrically coupled (e.g., welded or crimped) to inner coil L2, and covered by inner insulator tube 201. The front rim of inner conductive ring 704 is coupled to a base of an elongated conductive pin 706. Pin 706 may be held in place within inner conductive ring 704 by, for example, a first crimp C1. A second crimp may be provided at location C2 to bond outer contact ring 703 to front ring 702.

An overmolding process may be used to create a durable, insulating surface 709 over braided tube 701, rear ring 700 and front ring 702. The molding material (e.g., silicon rubber, or other suitable molding material) permeates the braided mesh to achieve a strengthened, mesh-reinforced cable of uniform diameter. Some known cable technologies apply an enlarged rubber structure such as a ball or a series of adjacent disks, to locally enhance the strength of a cable. Such a prior art technique may not be satisfactory in applications where a uniform cable diameter is desired. The permeated mesh tube can provide improved strength without such undesired expansions in cable size.

A molding process may also be used to form a contact insulator 707 that fills the interstices between outer contact ring 703 and inner conductive ring 704, as well as forming an umbrella-shaped seal catch 708 configured to engage umbrella-shaped seal 412 of the female connector. A silicon rubber to silicon rubber contact formed by seal 412 and seal catch 708 may provide for improved retention, as well as providing a more effective seal than the O-rings used in known pacemaker technology.

Another benefit of the umbrella-shaped seal is that it can be configured to provide for tactile feedback during connector insertion. As seal 412 and seal catch 708 pass each other during insertion, each may be gradually compressed until the umbrella "tips" clear each other. Upon clearance, the male and female elements of the umbrella-shaped seal snap back to a neutral (i.e., uncompressed) position. This snapping action may be felt as a "click", indicating to a surgeon that a satisfactory engagement of the male and female connectors has been achieved. The strength of the click and, to some extent, the insertion and retention force of the connectors may be controlled, in part, by the angles associated with the umbrella seal elements 412 and 708.

Figure 8:
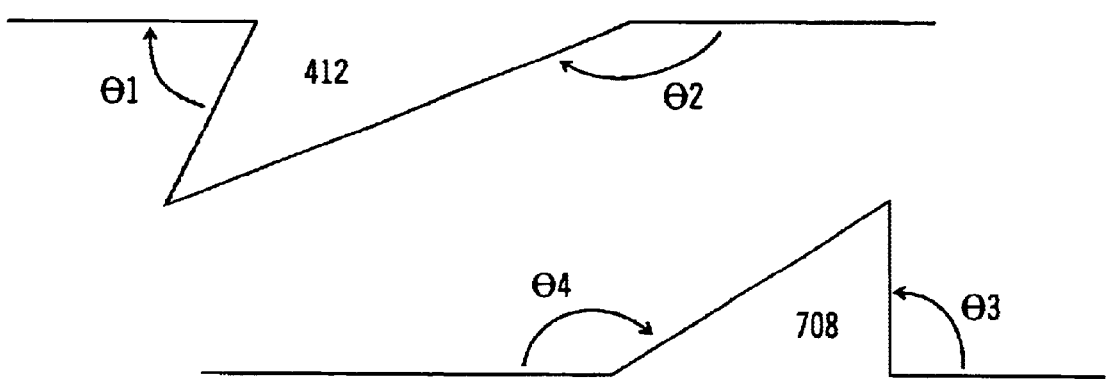
FIG. 8 is a close-up view of an umbrella seal in accordance with an embodiment of the invention.

FIG. 8 is a close-up side view of umbrella seal elements 412 and 708. The insertion force of the connectors may be dependent upon angles θ2 and θ4, decreasing with larger angles and increasing with smaller angles. The retention force may be dependent upon angles θ1 and θ3, as is the click strength. For example, according to one embodiment of the invention, θ1 and θ3 may vary between about 60+ and 90° depending on the amount of retention force. Retention strength and click strength increase as θ1 and θ3 get smaller. A trade-off may be made between improved retention and click strength versus the number of insertions that can be made, on average, before seal failure occurs (e.g., through tearing of either element 412 or element 708).

Another manner in which retention force may be improved according to one embodiment is to define annular grooves within outer contact ring 703 and/or contact pin 706, as shown by element numbers 711 and 710, respectively. Grooves 710 and 711 engage contact springs 408 and 416, respectively. Insertion force remains unaffected, and tactile feedback may be improved by the engagement of each spring with its respective groove. Retention force may be increased by that amount of force needed to compress the springs for disengagement from the grooves.

Figure 9:
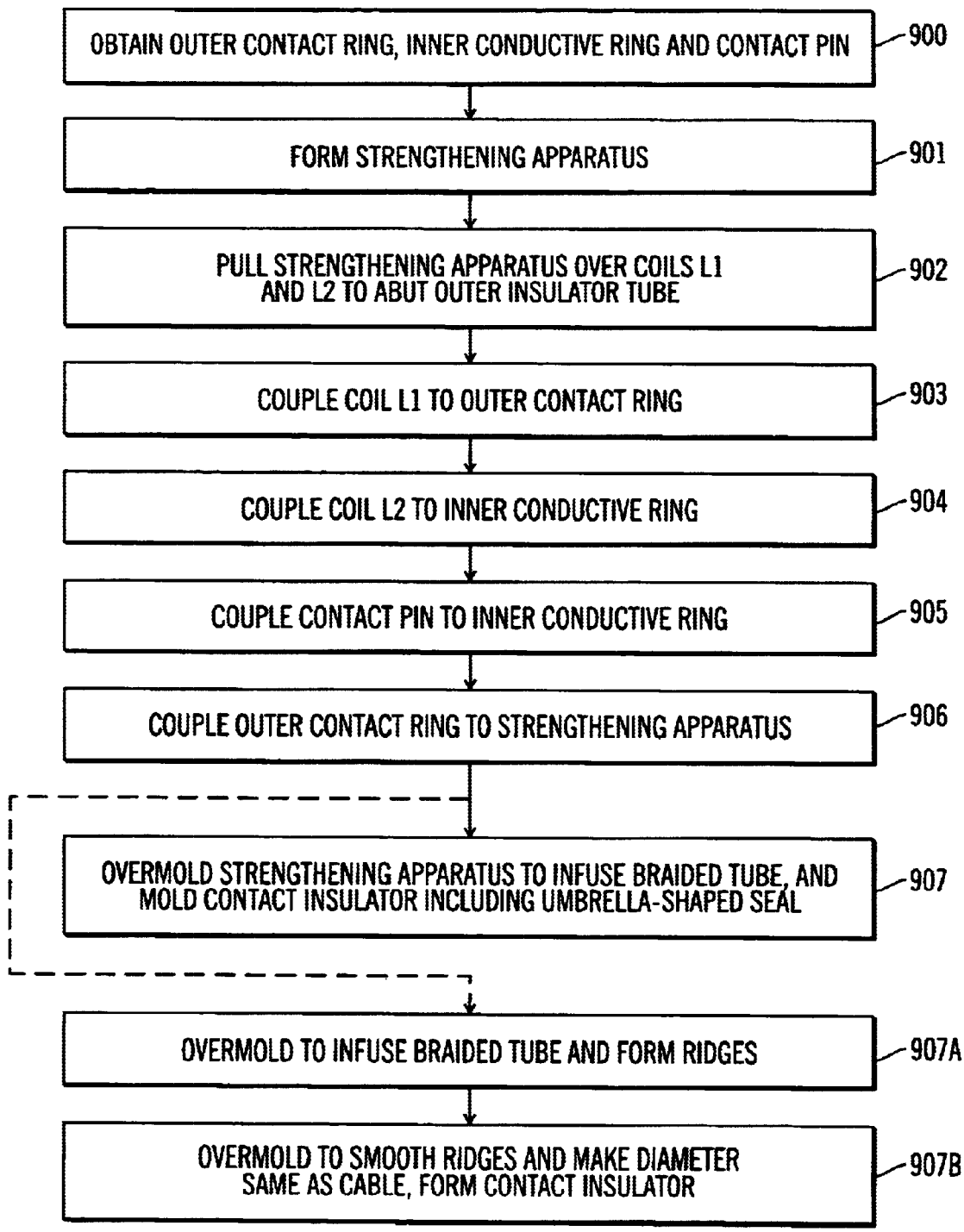
FIG. 9 is a flow diagram of a process for forming a male connector in accordance with an embodiment of the invention.

FIG. 9 is a flow diagram of a process for making the male connector shown in FIG. 7. It will be understood by one skilled in the art that certain steps in the disclosed process may be performed in different order or in parallel with other steps without departing from the scope of the invention. Also, other embodiments may be fabricated according to other procedures.

In step 900, outer contact ring 703, inner conductive ring 704 and contact pin 706 are obtained. Rings 703 and 704 and pin 706 may be machined from a generally rigid, conductive material, such as, but not limited to, steel, or they may be formed of other rigid materials and coated with a suitable conductive material. In step 901, the threads of braided tube 702 are coupled (e.g., spot-welded) to rear ring 700 and front ring 702 to form a cable strengthening apparatus. In step 902, coils L1 and L2 and inner insulator tube 201 are extended from outer insulator tube 202, and the strengthening apparatus formed by elements 700–702 is drawn over coils L1 and L2 and tube 201 until rear ring 700 abuts outer insulator tube 202.

With the strengthening apparatus in place, at step 903, outer contact ring 703 may be drawn over the inner insulator tube 201 (and coil L2). Outer coil L1 may be pulled around the exterior of the rearward rim of outer contact ring 703 and welded, or otherwise electrically coupled, to outer contact ring 703. The rearward rim of outer contact ring 703 may then be fitted inside of front ring 702.

In step 904 of FIG. 9, inner coil L2 and inner insulator tube 201 may be drawn through outer contact ring 703, where coil L2 may be wrapped around, and welded or crimped, or otherwise electrically coupled, to the rearward rim of inner conductive ring 704. Inner insulator tube 201 is pulled over coil L2 and the rearward rim of inner contact ring 704 to abut a raised central portion of ring 704. In step 905, contact pin 706 is inserted into the forward rim of inner conductive ring 704 and fixed in place with crimp C1. With contact pin 706 attached to inner conductive ring 704, contact pin 706 may be pushed back into outer contact ring 703 until inner conductive ring 704 is centered inside of outer contact ring 703 as shown in FIG. 7. In step 906, outer contact ring 703, braided tube 701 and front ring 702 may be joined via crimp C2.

In step 907, a rubber overmolding process infuses braided tube 701 and fill region 709 to generally the same diameter as the sensor cable (i.e., outer insulator tube 202). This overmolding process also forms contact insulator 707, including umbrella-shaped seal catch 708. If a single overmolding pass is insufficient to completely infuse mesh tube 701 and achieve a uniform diameter with outer insulator tube 202, a two pass overmolding process may be implemented. For example, in one possible two-pass embodiment, in a first pass 907A, braided tube 701 may be infused with rubber, and a ribbed pattern formed in region 709, preferably to the diameter of outer insulator tube 202. Then, in a second pass 907B, the ribbed pattern may be overmolded once again to form a smooth cylindrical surface of uniform diameter. Contact insulator 707 may be formed in either one of overmolding passes 907A and 907B.

Figure 10:
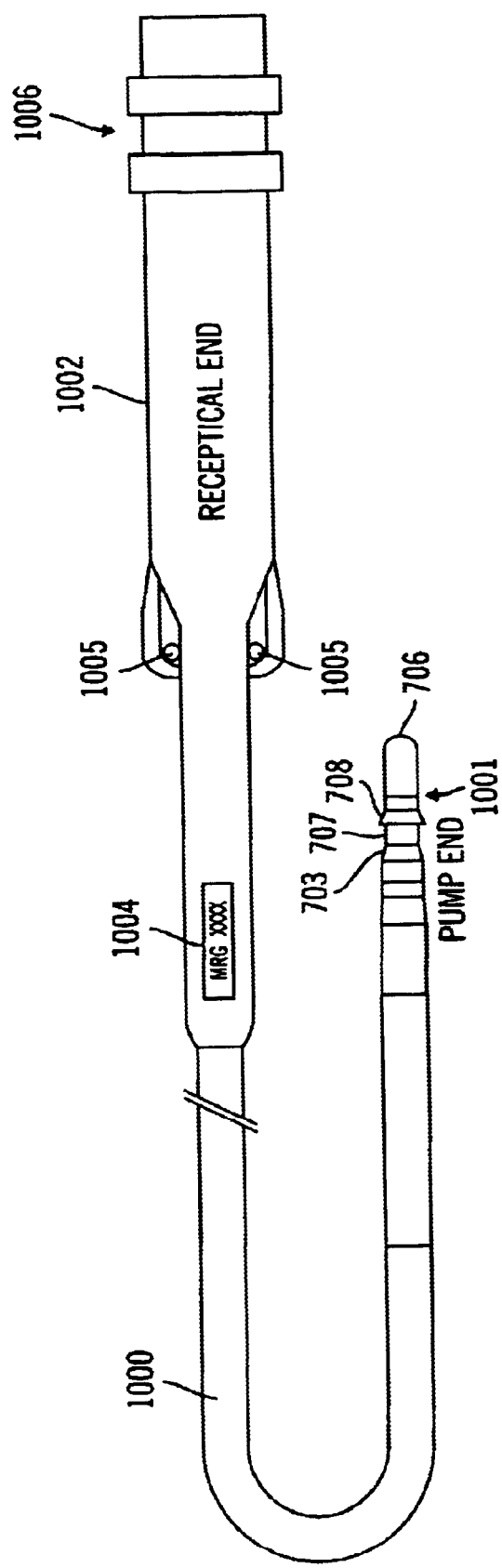
FIG. 10 is a plane view of a sensor lead having male and female connectors configured in accordance with an embodiment of the invention.

FIG. 10 is a view of a completed sensor lead in accordance with an embodiment of the invention. The sensor lead comprises sensor lead cable 1000, male connector 1001 and female connector 1002. Visible elements of male connector 1001 include outer contact ring 703, contact insulator 707 with umbrella-shaped seal catch 708, and contact pin 706. Visible elements of female connector 1002 include label 1004, suture holes 1005 and suture rings 1006.

III. Method and Apparatus for Insertion of Sensor Lead

Figure 11:
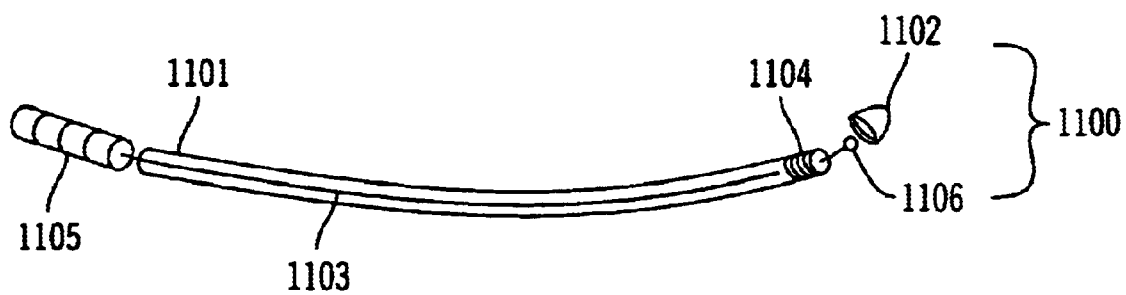
FIG. 11 is a cross-sectional view of a tunnel tool for inserting an implantable lead in accordance with an embodiment of the invention.

In accordance with an embodiment of the invention, the sensor lead may be implanted in the patient through the use of a tunneling tool such as tool 1100 shown in FIG. 11. It will be understood by one skilled in the art that the sensor lead may be implanted or otherwise utilized in some applications without the employment of such a tunneling tool. However, tool 1100 provides a mechanism that minimizes the physically invasive nature of the implantation procedure for the patient, and protects the sensor lead from excessive stresses during insertion.

A. Tunneling Tool

As shown in FIG. 11, tool 1100 comprises an elongated, hollow tube structure 1101, having a removable, bullet-shaped member or endpiece 1102, and a pull rod 1103 designed to fit within the hollow bore of tube 1101. Tube 1101 may be configured to span from a first incision near a first implant apparatus, such as a pump, out to and slightly beyond a second incision near a second implant apparatus, such as a sensor. In one embodiment, tube 1101 may be slightly curved along its length, to provide the surgeon with greater control during insertion. However, other embodiments may similarly employ a straight tube 1101. The length and curve of tube 1101 may vary for different implant procedures and for operating variables such as, but not limited to, patient body types (e.g., small child vs. large adult).

The diameter of the inner bore of tube 1101 may be of a size to accommodate the sliding movement through tube 1101 of the pull rod 1103 and the sensor lead (e.g., from the male end). A sensor lead with a uniform diameter for the cable and male connector may provide for easier passage of the sensor lead through tube 1101 with reduced minimum tolerances for the spacing between the sensor lead and the inner surface of tube 1101.

The thickness of the walls of tube 1101 may be designed to provide the rigidity necessary for a surgeon to manually guide tube 1101 through the fatty tissue of a patient, and may be a function of the strength of the material used to fashion the tube. In one embodiment, tube 1101 may be fashioned of steel. However, the tube material may be any rigid material suited to surgical procedures. Stronger materials allow for thinner tube walls, and thus smaller tube diameter. A smaller diameter may be desirable to minimize the trauma to the tissue through which the tube will be passed.

One end of tube 1101 may be equipped with a mechanism 1104 for engaging the open end of bullet-shaped endpiece 1102. One such mechanism, in accordance with an embodiment of the invention, may be the formation of threads on one end of tube 1101 upon which bullet-shaped endpiece 1102 may be screwed on or off. Endpiece 1102 is preferably shaped like a bullet to provide a point that will pierce and penetrate the subcutaneous fatty tissue of the patient without breaching the patient's skin tissue between incision points. However, it will be understood that other shapes may also be used without departing from the scope of the invention.

Pull rod 1103 comprises a slender rod having a first end preferably (though not necessarily) equipped with a handle 1105, and a second end having a ring 1106 or other connector mechanism for engaging the male end of a sensor lead. In one embodiment, ring 1106 engages the umbrella seal ridge of the male connector of a sensor lead. Pull rod 1103 is of a sufficient length relative to tube 1101 for ring 1106 to be exposed beyond the threaded end of tube 1101 when endpiece 1102 is removed.

B. Insertion Process

Figure 13:
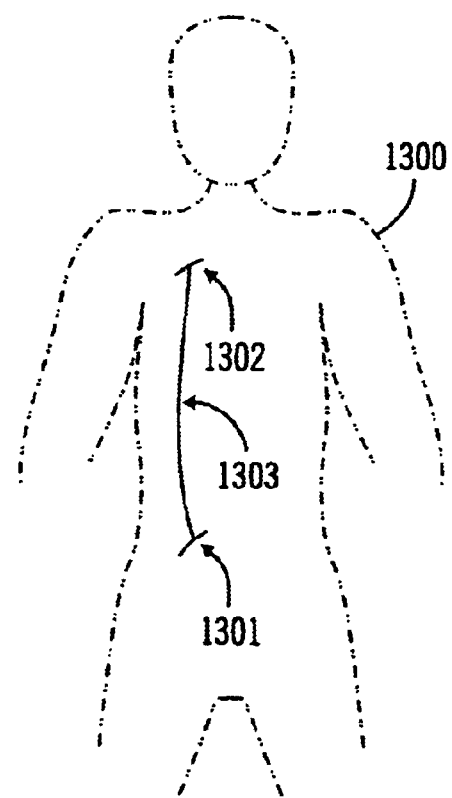
FIG. 13 is a frontal view of a human body prepared for the implant process of FIG. 12.
Figure 12:
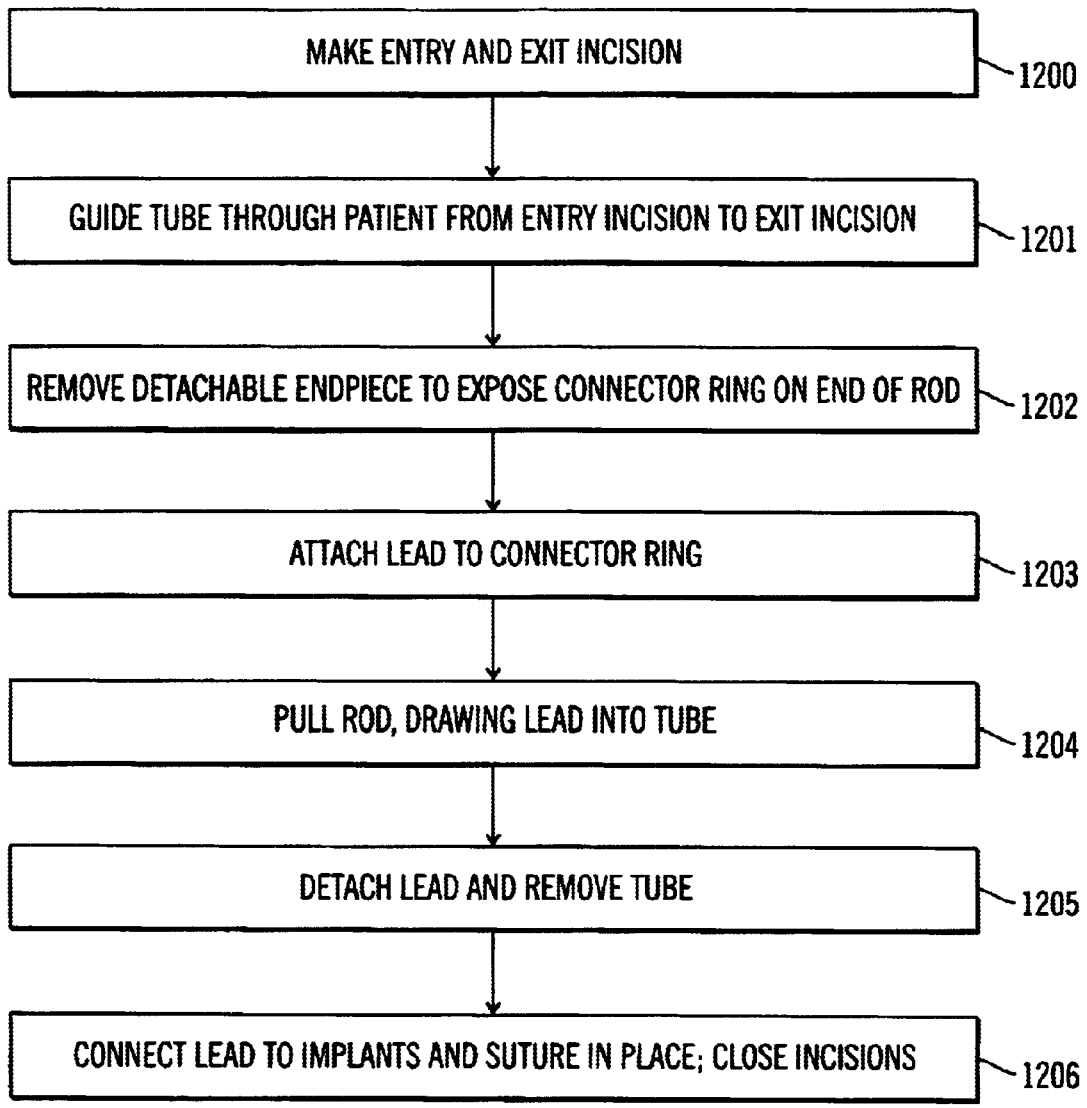
FIG. 12 is a flow diagram of a process for implanting a cable using a tunneling tool in accordance with an embodiment of the invention.

FIG. 12 is a flow diagram of the insertion procedure in accordance with one embodiment of the invention. It will be understood by one skilled in the art that certain steps in the disclosed process may be performed in different order or in parallel with other steps without departing from the scope of the invention. Also, other embodiments may accomplish insertion through other procedures. The steps of the insertion procedure are described, for illustrative purposes, with reference to the body diagram of FIG. 13. FIG. 13 is a general frontal view of a human body 1300 to be implanted with a sensor lead for a sensor/pump configuration. It will be understood that the procedure described is not limited to the sensor/pump example, but may apply to other lead implant operations.

In FIG. 13, incision 1301 corresponds, for example, to the approximate location in the lower abdomen of body 1300 where a female connector port for an implant device such as a pump may be located. Incision 1302 corresponds, for example, to the approximate location in the upper chest where a male connector port of an implant device such as a sensor may be located. Path 1303 represents the path of the tunneling tool and sensor lead through the fatty tissue of body 1300 from incision 1301 to incision 1302.

In step 1200 of FIG. 12, the surgeon makes incision 1301 near the port connector of the pump implanted near the pancreatic cavity in the patient's abdomen. A similar incision 1302 may be made in the upper chest of the patient near the port connector of the implanted sensor. In step 1201, tool 1100 may be inserted into lower incision 1301, leading with the attached bullet-shaped endpiece 1102. Following path 1303 through the patient's body 1300, the surgeon manually guides tool 1100 through the fatty tissue, under the skin of the patient, until bullet-shaped endpiece 1102 protrudes out of upper incision 1302. With tool 1100 in place along path 1303 under the patient's skin, at step 1202, endpiece 1102 may be removed (e.g., unscrewed) from the protruding end of tube 1101, exposing connector ring 1106 at the end of rod 1103.

With connector ring 1106 exposed, in step 1203, the male connector of the sensor lead is attached to connector ring 1106. In step 1204, the surgeon pulls on handle 1105, drawing rod 1103 out of tube 1101, and, consequently, drawing the sensor lead into tube 1101. At step 1205, once the connector ring 1106 is outside of tube 1101, the male connector of the sensor lead may be detached from connector ring 1106, and tube 1101 may be withdrawn from the patient's body, leaving the sensor lead within the patient's body 1300. At step 1206, with the sensor lead in the desired position, the sensor lead connectors may be coupled to the respective implant device connectors and sutured into position. The incisions are then closed.

In one embodiment, rod 1103 may be present within tube 1101 during insertion steps 1201 and 1202. However, in another embodiment, alternatively, rod 1103 may be threaded through tube 1101 upon completion of step 1202. Rod 1103 may be passed into either end of tube 1101 (and tube 1101 may be inserted through either incision), depending on which implant device connector (male or female) may be near which end of the rod.

In yet a further embodiment, bullet-shaped endpiece 1102 may be used to implement the handle of rod 1103, in which case rod 1103 may be fixed to the inner surface of endpiece 1102 and connector ring 1106 may be exposed at the opposite end of tube 1101. Rod 1103 can then be drawn through tube 1101 by detaching endpiece 1102 from tube 1101, attaching the sensor lead to connector ring 1106, and using endpiece 1102 as a handle to pull rod 1103 through tube 1101.

Several embodiments of the insertion tool and process have been described. Various embodiments share the advantages earlier described, such as minimizing operating complexity and patient risk during implant operations. Though especially advantageous when used in conjunction with the earlier described connector embodiments, it will be understood by one skilled in the art that the insertion tool and process are not limited to such connector embodiments.

Thus, a sensor lead for a medical implant device, a method of making such a lead, and a method and apparatus for inserting such a lead have been described in conjunction with one or more embodiments. The foregoing description of embodiments of the invention has been presented for the purposes of illustration and description. It is not intended to be exhaustive or to limit the invention to the precise form disclosed. Many modifications and variations may be possible in light of the above teaching. The invention is defined by the following claims and their full scope of equivalents.

What is claimed is:

1. An electrical connecting system comprising:
   a first connector having an electrically conductive element and an electrically conductive surface and an insulating member configured to electrically insulate the conductive element from said conductive surface;

a second connector comprising:
  a connector body defining an inner cavity with a first end and a second end, wherein said inner cavity is open at said first end, said inner cavity configured to receive said first connector;
  a first electrically conductive tension member within said inner cavity, said first conductive tension member configured to engage said conductive element to form a first electrical channel; and
  a second electrically conductive tension member within said inner cavity, said second conductive tension member configured to engage said conductive surface to form a second electrical channel.

2. The system of claim 1, wherein said second connector has an insertion force of no greater than fourteen Newtons with respect to said first connector.

3. The system of claim 1, wherein said second connector has a retention force of at least five Newtons with respect to said first connector.

4. The system of claim 1, wherein said first connector and said second connector are configured for unidirectional mechanical engagement.

5. The system of claim 1, wherein:
  the second connector further comprises a first seal within said inner cavity, said first seal configured to engage said insulating member to isolate said first electrical channel from said second electrical channel.

6. The system of claim 5, wherein:
  said first seal comprises an umbrella-shaped ridge; and
  said insulating member comprises a seal catch configured to engage said umbrella-shaped ridge.

7. The system of claim 6, wherein said first seal and said seal catch form a tactile feedback mechanism.

8. The system of claim 5, wherein said second connector further comprises a second seal configured to engage said first connector to isolate said inner cavity.

9. The system of claim 8, wherein said second seal comprises an annular ring of flexible material, said annular ring having a plurality of annular ridges that contact said first connector while said first connector is within said inner cavity.

10. The system of claim 9, wherein said flexible material is molded rubber.

11. The system of claim 8, wherein said second seal is located within a first annular groove substantially adjacent to said first end of said inner cavity.

12. The system of claim 5, wherein said connector body comprises:
  a first conductive body member defining said first end of said inner cavity;
  a second conductive body member defining said second end of said inner cavity; and
  a middle insulator coupled between said first conductive body member and said second conductive body member.

13. The system of claim 12, wherein said first conductive body member is comprised of steel.

14. The system of claim 12, wherein said second conductive body member is comprised of steel.

15. The system of claim 12, wherein said middle insulator is comprised of a resilient, nonconductive material.

16. The system of claim 15, wherein said resilient, nonconductive material is polysulfone.

17. The system of claim 12, wherein the interior of said first conductive body member comprises an annular groove wherein said first conductive tension member is located.

18. The system of claim 17, wherein said second connector further comprises a wear-resistant member fitted into said annular groove between said first conductive tension member and said middle insulator.

19. The system of claim 18, wherein said wear resistant member comprises a washer.

20. The system of claim 17, wherein said first conductive tension member comprises a toroidal spring.

21. The system of claim 12, wherein said middle insulator comprises an annular groove in which said first seal is seated.

22. The system of claim 12, wherein the interior of said second conductive body member comprises an annular groove wherein said second conductive tension member is located.

23. The system of claim 22, wherein said second connector further comprises a wear-resistant member fitted into said annular groove between said second conductive tension member and said middle insulator.

24. The system of claim 23, wherein said wear resistant member comprises a washer.

25. The system of claim 24, wherein said second conductive tension member comprises a toroidal spring.

26. The system of claim 12, further comprising a two-conductor electrical cable coupled to said second connector.

27. The system of claim 26, wherein said cable comprises:
  an outer coil comprising a first helical ribbon conductor;
  an inner coil within said outer coil, said inner coil comprising a second helical ribbon conductor;
  an inner insulating tube between said inner coil and said outer coil; and
  an outer insulating tube encompassing said outer coil.

28. The system of claim 27, wherein said first helical ribbon conductor comprises a plurality of adjacent conductive wires configured in a ribbon strip that is twisted about a central axis to form a helix.

29. The system of claim 28, wherein each of said conductive wires comprises a silver core surrounded by a cobalt alloy layer.

30. The system of claim 28, wherein said ribbon strip is configured to have a maximum distance by which any one of said plurality of adjacent wires may be offset from said ribbon strip.

31. The system of claim 27, wherein:
  said inner coil is coupled to said first conductive body member;
  said outer coil wraps around an exterior surface of said connector body; and
  said outer coil is electrically coupled to an external surface of said second conductive body member.

32. The system of claim 31, further comprising an electrically insulating layer around said exterior surface of said connector body and said outer coil.

33. The system of claim 32 applied to an implant patient, wherein said insulating layer comprises means for suturing said second connector within said implant patient.

34. The system of claim 1, further comprising a two-conductor electrical cable coupled to said first connector.

35. The system of claim 34, wherein said cable is coupled to said first connector through a braided tube adjacent to said first connector.

36. The system of claim 35, wherein said braided tube is infused with a flexible insulating material.

37. The system of claim 36, wherein said braided tube is overmolded with said flexible insulating material to have about the same diameter as said cable.

38. The system of claim 37, wherein said first connector has a diameter less than or about equal to the diameter of said cable.

39. The system of claim 35, wherein said braided tube comprises a steel mesh.

40. The system of claim 34, wherein said cable comprises:
an outer coil comprising a first helical ribbon conductor;
an inner coil within said outer coil, said inner coil comprising a second helical ribbon conductor;
an inner insulating tube between said inner coil and said outer coil; and
an outer insulating tube encompassing said outer coil.

41. The system of claim 40, wherein said first helical ribbon conductor comprises a plurality of adjacent conductive wires configured in a ribbon strip that is twisted about a central axis to form a helix.

42. The system of claim 41, wherein each of said conductive wires comprises a silver core surrounded by a cobalt alloy layer.

43. The system of claim 41, wherein said ribbon strip is configured to have a maximum distance by which any one of said plurality of adjacent wires may be offset from said ribbon strip.

44. The system of claim 40, wherein said inner coil is coupled to said conductive element and said outer coil is coupled to said conductive surface.

45. A female connector for receiving a male connector having an electrically conductive element and an electrically conductive surface, comprising:
a connector body defining an inner cavity with a first end and a second end, wherein said inner cavity is open at said first end, said inner cavity configured to receive said male connector;
a first electrically conductive tension member within said inner cavity, said first conductive tension member configured to engage said conductive element to form a first electrical channel;
a second electrically conductive tension member within said inner cavity, said second conductive tension member configured to engage said conductive surface to form a second electrical channel; and
a first seal within said inner cavity, said first seal configured to engage said male connector to isolate said first electrical channel from said second electrical channel;
wherein said first seal comprises an umbrella-shaped ridge.

46. The female connector of claim 45 having an insertion force of no greater than fourteen Newtons with respect to said male connector.

47. The female connector of claim 45 having a retention force of at least five Newtons with respect to said male connector.

48. The female connector of claim 45 being mechanically unidirectional with respect to said male connector.

49. The female connector of claim 45, wherein said umbrella-shaped ridge has a forward angle and a rearward angle.

50. The female connector of claim 45, wherein said first seal is a tactile feedback mechanism.

51. A female connector for receiving a male connector having an electrically conductive element and an electrically conductive surface, comprising:
a connector body defining an inner cavity with a first end and a second end, wherein said inner cavity is open at said first end, said inner cavity configured to receive said male connector;
a first electrically conductive tension member within said inner cavity, said first conductive tension member configured to engage said conductive element to form a first electrical channel;
a second electrically conductive tension member within said inner cavity, said second conductive tension member configured to engage said conductive surface to form a second electrical channel;
a first seal within said inner cavity, said first seal configured to engage said male connector to isolate said first electrical channel from said second electrical channel; and
a second seal configured to engage said male connector to isolate said inner cavity
wherein said first seal comprises an umbrella-shaped ridge and said second seal comprises an annular ring of flexible material, said annular ring having a plurality of annular ridges.

52. The female connector of claim 51, wherein said flexible material is molded rubber.

53. The female connector of claim 52, wherein said second seal is located within a first annular groove substantially adjacent to said first end of said inner cavity.

54. A female connector for receiving a male connector having an electrically conductive element and an electrically conductive surface, comprising:
a connector body defining an inner cavity with a first end and a second end, wherein said inner cavity is open at said first end, said inner cavity configured to receive said male connector;
a first electrically conductive tension member within said inner cavity, said first conductive tension member configured to engage said conductive element to form a first electrical channel;
a second electrically conductive tension member within said inner cavity, said second conductive tension member configured to engage said conductive surface to form a second electrical channel; and
a first seal within said inner cavity, said first seal configured to engage said male connector to isolate said first electrical channel from said second electrical channel;
wherein said connector body comprises:
a first conductive body member defining said first end of said inner cavity;
a second conductive body member defining said second end of said inner cavity; and
a middle insulator coupled between said first conductive body member and said second conductive body member.

55. The female connector of claim 54, wherein said first conductive body member is comprised of steel.

56. The female connector of claim 54, wherein said second conductive body member is comprised of steel.

57. The female connector of claim 54, wherein said middle insulator is comprised of a resilient, nonconductive material.

58. The female connector of claim 57, wherein said resilient, nonconductive material is polysulfone.

59. The female connector of claim 58, wherein the interior of said first conductive body member comprises an annular groove wherein said first conductive tension member is located.

60. The female connector of claim 59, further comprising a wear-resistant member fitted into said annular groove between said first conductive tension member and said middle insulator.

61. The female connector of claim 60, wherein said wear resistant member comprises a washer.

62. The female connector of claim 59, wherein said first conductive tension member comprises a toroidal spring.

63. The female connector of claim 54, wherein said middle insulator comprises an annular groove in which said first seal is seated.

64. The female connector of claim 54, wherein the interior of said second conductive body member comprises an annular groove wherein said second conductive tension member is located.

65. The female connector of claim 64, wherein said second connector further comprises a wear-resistant member fitted into said annular groove between said second conductive tension member and said middle insulator.

66. The female connector of claim 54, wherein said wear resistant member comprises a washer.

67. The female connector of claim 66, wherein said second conductive tension member comprises a toroidal spring.

68. The female connector of claim 54, further comprising a two-conductor electrical cable coupled to said second connector.

69. The female connector of claim 68, wherein said cable comprises:
   an outer coil comprising a first helical ribbon conductor;
   an inner coil within said outer coil, said inner coil comprising a second helical ribbon conductor;
   an inner insulating tube between said inner coil and said outer coil; and
   an outer insulating tube encompassing said outer coil.

70. The female connector of claim 69, wherein said first helical ribbon conductor comprises a plurality of adjacent conductive wires configured in a ribbon strip that is twisted about a central axis to form a helix.

71. The female connector of claim 70, wherein each of said conductive wires comprises a silver core surrounded by a cobalt alloy layer.

72. The female connector of claim 69, wherein said ribbon strip is configured to have a maximum distance by which any one of said plurality of adjacent wires may be offset from said ribbon strip.

73. The female connector of claim 69, wherein:
   said inner coil is coupled to said first conductive body member;
   said outer coil wraps around an exterior surface of said connector body; and
   said outer coil is electrically coupled to an external surface of said second conductive body member.

74. The female connector of claim 73, further comprising an electrically insulating layer around said exterior surface of said connector body and said outer coil.

75. The female connector of claim 74 applied to an implant patient, wherein said insulating layer comprises means for suturing said second connector within said implant patient.

* * * * *